US00PP20343P2

(12) United States Plant Patent
Snoeijer

(10) Patent No.: US PP20,343 P2
(45) Date of Patent: Sep. 22, 2009

(54) ***CLEMATIS* PLANT NAMED 'ZOJAPUR'**

(50) Latin Name: *Clematis hybrid*
Varietal Denomination: Zojapur

(76) Inventor: Wim Snoeijer, Vest 162, 2801 TX Gouda (NL)

( * ) Notice: Subject to any disclaimer, the term of this patent is extended or adjusted under 35 U.S.C. 154(b) by 0 days.

(21) Appl. No.: 12/228,016

(22) Filed: Aug. 8, 2008

(51) Int. Cl.
*A01H 5/00* (2006.01)

(52) U.S. Cl. ..... Plt./228
(58) Field of Classification Search ..... Plt./228
See application file for complete search history.

*Primary Examiner*—June Hwu
(74) *Attorney, Agent, or Firm*—Penny J. Aguirre

(57) ABSTRACT

A new cultivar of hybrid *Clematis*, 'Zojapur', characterized by its nodding open campanulate-shaped flowers that are deep purple in color with lighter red-purple centers, its free flowering habit in spring with free flowering re-bloom in summer when pruned, its climbing growth habit, and its cold hardiness to U.S.D.A. Zone 5.

3 Drawing Sheets

Botanical classification: *Clematis* hybrid.
Variety denomination: 'Zojapur'.

BACKGROUND OF THE INVENTION

The present invention relates to a new and distinct cultivar of *Clematis*, botanically of hybrid origin and classified in the Jackmanii Group, and will be referred to hereafter by its cultivar name, 'Zojapur'. 'Zojapur' is grown as an herbaceous climber for landscape use and for use as a flowering potplant for the terrace.

'Zojapur' derived from an ongoing breeding program by the inventor in his nursery in Boskoop, The Netherlands. The goal of the selection was to select a hardy climber with uniquely colored flowers that could be grown for different purposes in the garden. 'Zojapur' was selected in summer of 2003 and arose from a controlled cross made in 1999 between the female parent, *Clematis* 'Mrs. George Jackman' (not patented) and the male parent, *Clematis* 'Walenburg' (not patented).

Asexual reproduction of the new cultivar was first accomplished by internodial stem cuttings under the direction of the inventor in Boskoop, The Netherlands in 2003. The characteristics of this cultivar have been determined to be stable and are reproduced true to type in successive generations.

SUMMARY OF THE INVENTION

The following traits have been repeatedly observed and represent the characteristics of the new cultivar as grown outdoors 'Zojapur' from other cultivars of *Clematis* known to the inventor.

1. 'Zojapur' exhibits nodding flowers that are deep purple in color with a center section that is lighter and red-purple in color.
2. 'Zojapur' is free flowering in spring and repeats its free flowering habit in summer when pruned after spring bloom.
3. 'Zojapur' exhibits a climbing growth habit.
4. 'Zojapur' is cold hardy to U.S.D.A. Zone 5.

'Zojapur' differs from its female parent, 'Mrs. George Jackman', in having purple colored flowers rather than white and in having a stronger habit and differs from its male parent, 'Walenburg' in having much larger flowers and flowers that are purple in color rather than mauve pink. Close comparisons are *Clematis* 'Jackmanii' and 'Star of India' (both unpatented). 'Jackmanii' differs from 'Zojapur' in having flowers that are more violet-blue in color with tepals that are less rounded and have a dark purple tint at the base. 'Star of India' differs in having flowers that are violet-blue in color with red-purple centers, tepals with a dark purple tint at the base and stamens that are twisted.

BRIEF DESCRIPTION OF THE DRAWING

The accompanying colored photographs illustrate the overall appearance and distinct characteristics of the new *Clematis*. The photographs were taken of a plant of 'Zojapur' as grown in a trial bed for 3 years in Boskoop, The Netherlands.

The photograph in FIG. 1 shows the flowering habit.

Figure 1:
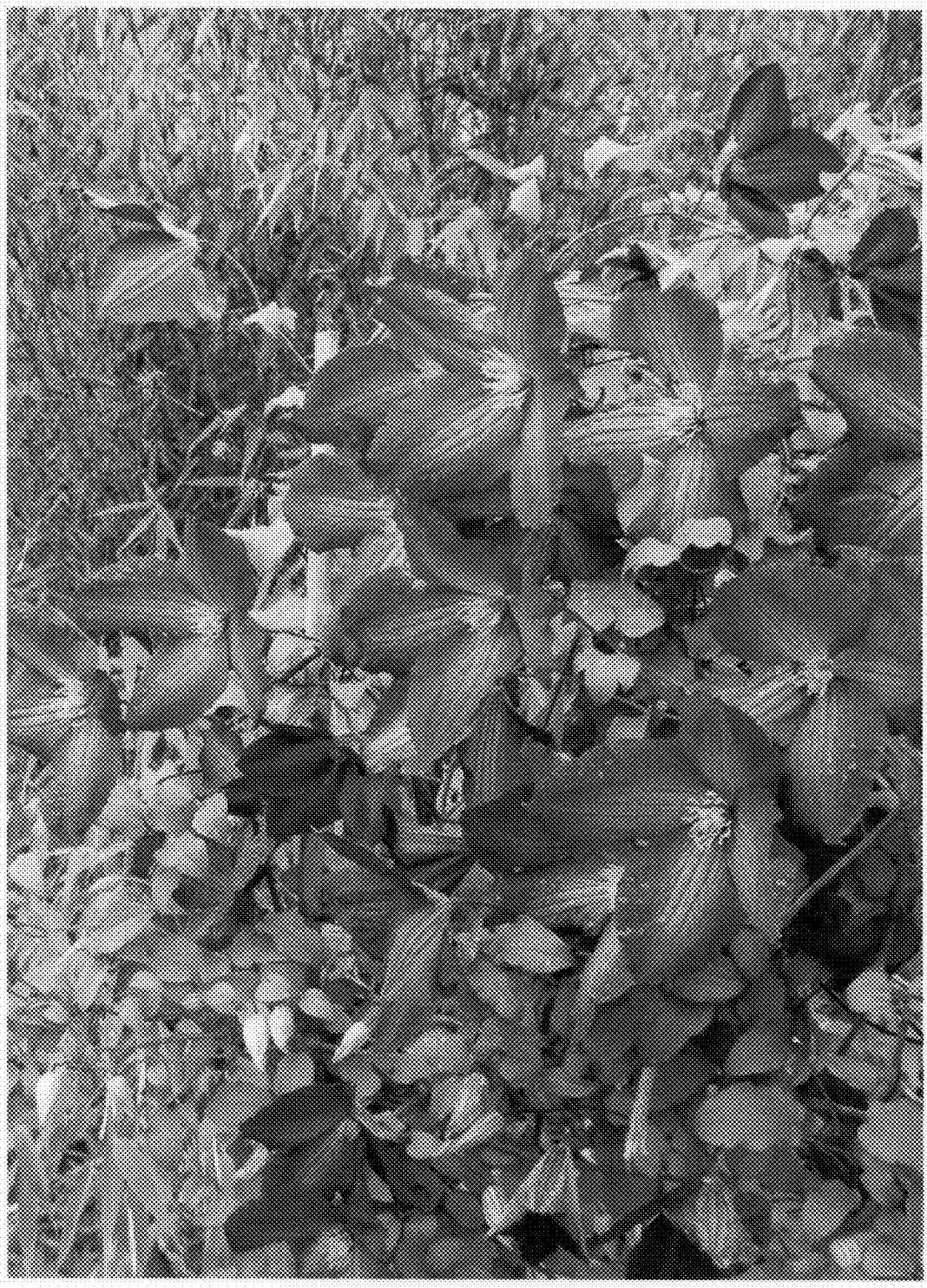
Figure 2:
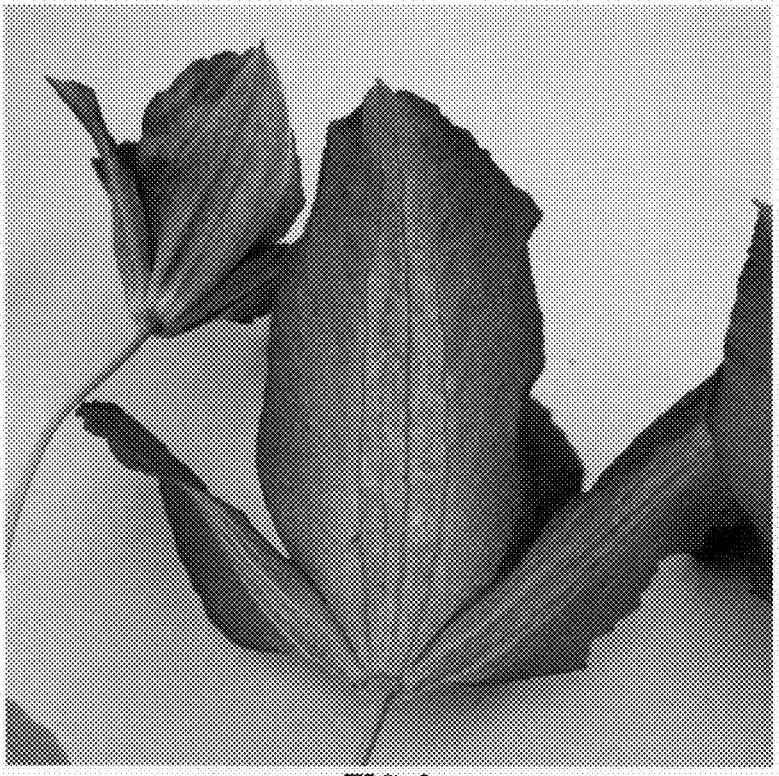

The photograph in FIG. 2 provides a close-up view of the outer surface of the flower and flower form.

Figure 3:
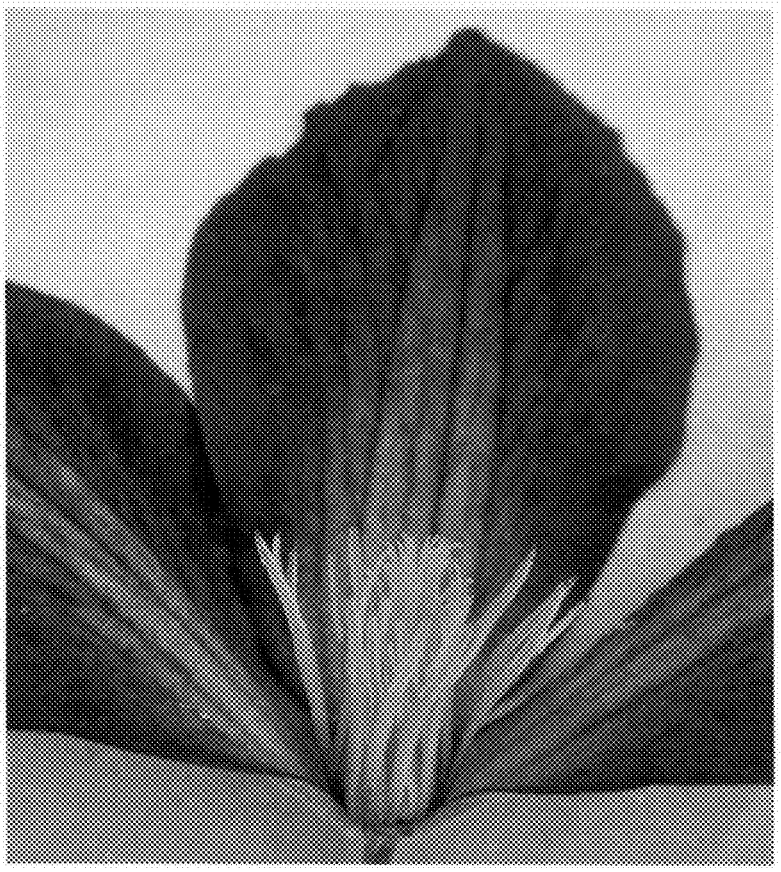

The photograph in FIG. 3 provides a close-up view of the upper surface of the flower and pistils and stamens (one tepal is removed).

Figure 4:
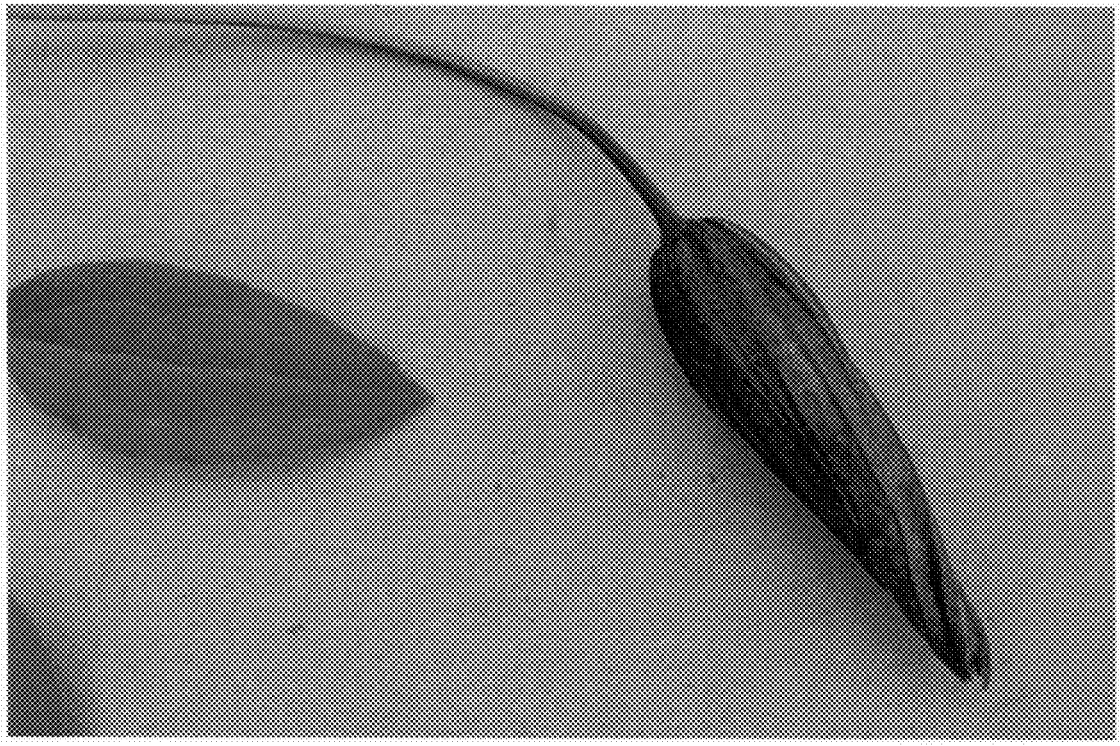

The photograph in FIG. 4 provides a view of a flower bud and leaf.

Figure 5:
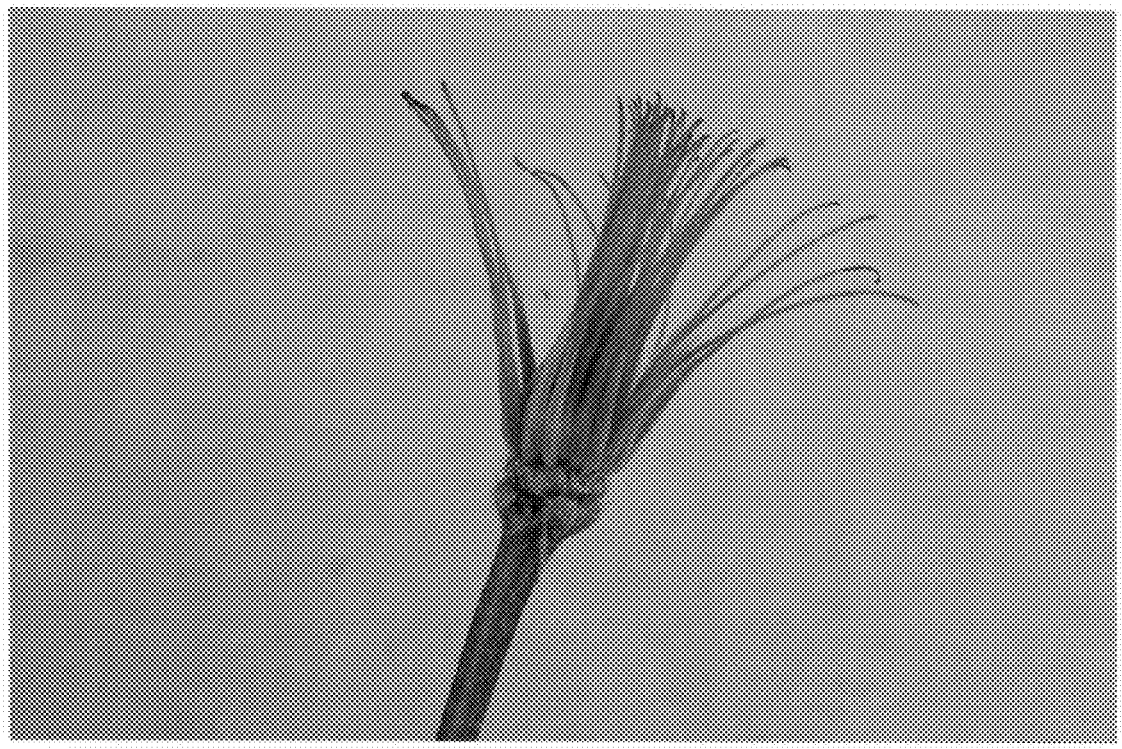

The photograph in FIG. 5 provides a close-up view of a seedhead.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of 3 year-old plants of 'Zojapur' as grown outdoors in full sun to semi-shade in a test plot in Boskoop, The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Zojapur' is classified in the Jackmanii Group of *Clematis*.

*Blooming period.*—Free flowering for about 4 weeks in spring and blooms again in summer if pruned after spring bloom.

*Plant habit.*—Herbaceous climber.

*Height and spread.*—Three year-old plant is about 15 cm at base with a height of about 2 m when pruned after spring flowering.

*Cold hardiness.*—U.S.D.A. Zone 5.

*Culture.*—Moist but well-drained soils in full sun with roots shaded.

*Diseases.*—No particular resistance to diseases has been observed.

*Root description.*—Fleshy.

Growth and propagation:

*Propagation.*—Internodial softwood cuttings from vegetative shoots.

*Root initiation.*—Roots develop in 6 weeks in summer under greenhouse conditions.

*Time required for root development.*—75 to 90 days to develop a 5 cm container from a 5 cm cutting.

*Growth rate.*—Moderately vigorous once planted in the landscape.

Stem description:

*Shape.*—Round and 6 ribbed.

*Stem color.*—Lower surface 143C, upper surface 143C with tint of 59C, matures to 175B.

*Stem size.*—About 2 m (including peduncle and terminal pedicel) in length, average of 4.5 mm in diameter.

*Stem surface.*—Sparsely covered with hairs.

*Internode length.*—Ranges from 4 to 15 cm.

*Branching.*—Basal branching.

Foliage description:

*Leaf arrangement.*—Opposite.

*Leaf division.*—Odd-pinnate and becoming ternate at upper portion of shoot.

*Leaflet shape.*—Broadly lanceolate.

*Leaflet base.*—Cuneate.

*Leaflet apex.*—Acuminate.

*Leaflet fragrance.*—None.

*Leaflet venation.*—Primarily reticulate, not prominent, 144C in color.

*Leaflet margins.*—Entire.

*Leaflet attachment.*—Petioluled with leaf petioled.

*Leaflet surface.*—Upper surface glabrous and lower surface is glossy and covered with sparse hairs.

*Leaflet size.*—Up to 10 cm in length and 5 cm in width.

*Leaflet color.*—Upper surface 146C, lower surface 147C.

*Petioles and petiolules.*—5 to 10 cm in length and about 1.5 mm in width, round in shape, 146C in color, sparsely hairy surface.

Inflorescence description:

*Inflorescence type.*—Solitary or 3 to 5 flowered dichasial cyme.

*Inflorescence arrangement.*—Terminal and axillary on young shoots.

*Peduncles.*—3 to 6 cm in length and an average of 2 mm in width, 146C in color, surface sparsely covered with short hairs and ribbed, bracts; leaf-like, simple, lanceolate in shape, about 1 to 5 cm in length and 0.7 to 3.5 cm in width, color and surface is the same as leaflets.

*Pedicels.*—3 to 11 cm in length and an average of 2 mm in width, 146C in color with tint of 83A towards the flower, surface sparsely covered with hairs.

*Bud description.*—Nodding, lanceolate in shape with tip slightly twisted, about 4 cm in length and 1.5 cm in width, 86A in color on tepal margins with other areas a blend of 86A to 86D, hairy surface and tomentose on tepal margins.

*Flower fragrance.*—None.

*Lastingness of flowers.*—Individual flowers last about 7 days, tepals drop prior to stamens.

*Flower quantity.*—About 150 flowers on a 3 year-old plant.

*Flower type.*—Open campanulate.

*Flower aspect.*—Horizontal to slightly nodding.

*Flower size.*—Range from 6 to 8 cm in diameter and about 6 cm in depth.

*Tepal number.*—4, less commonly 5.

*Tepal shape.*—Obovate.

*Tepal apex.*—Acute to obtuse.

*Tepal base.*—Cuneate.

*Tepal margins.*—Entire.

*Tepal surface.*—Upper surface is glabrous, lower surface is tomentose with center and margins glabrous.

*Tepal color.*—Upper surface; 79B near margin, N80A in centers area and blending to N82C near base, veins 79B, lower surface; N92D margin, blend of 94B to 94D in center area, veins 93B.

*Tepal size.*—Up to 6 cm in length and 4 cm in width.

Reproductive organs:

*Gynoecium.*—Numerous pistils (about 50), 1.5 cm in length, style is 150D with hairs 165C near base, ovary is superior, hairy and143C in color.

*Androcoecium.*—Stamens (about 40), filaments are 0.3 to 1 cm in length and 0.8 mm in width, glabrous, and 144D in color with base N89C, anthers are 0.4 cm in length, linear in shape and 144D in color, connective is 144B in color with tiny mucronate tip, pollen is moderate in quanfity and 4C in color.

*Seed.*—Seed heads are comprised of drying anthers, however seed production has not been observed.

It is claimed:

1. A new and distinct cultivar of *Clematis* plant named 'Zojapur' as herein illustrated and described.

* * * * *